(12) United States Patent
Lundt

(10) Patent No.: US 10,786,220 B2
(45) Date of Patent: Sep. 29, 2020

(54) DEVICE FOR IMAGING AN OBJECT

(71) Applicant: KONINKLIJKE PHILIPS N.V., Eindhoven (NL)

(72) Inventor: Bernd Lundt, Flintbek (DE)

(73) Assignee: KONINKLIJKE PHILIPS N.V., Endhoven (NL)

( * ) Notice: Subject to any disclaimer, the term of this patent is extended or adjusted under 35 U.S.C. 154(b) by 126 days.

(21) Appl. No.: 15/772,604

(22) PCT Filed: Nov. 2, 2016

(86) PCT No.: PCT/EP2016/076314
§ 371 (c)(1),
(2) Date: May 1, 2018

(87) PCT Pub. No.: WO2017/076841
PCT Pub. Date: May 11, 2017

(65) Prior Publication Data
US 2019/0117183 A1 Apr. 25, 2019

(30) Foreign Application Priority Data
Nov. 4, 2015 (EP) ..................... 15192891

(51) Int. Cl.
*A61B 6/00* (2006.01)
*A61B 6/04* (2006.01)
(52) U.S. Cl.
CPC .............. *A61B 6/545* (2013.01); *A61B 6/487* (2013.01); *A61B 6/5211* (2013.01); *A61B 6/547* (2013.01)

(58) Field of Classification Search
CPC ....... A61B 6/487; A61B 6/5211; A61B 6/545; A61B 6/547
See application file for complete search history.

(56) References Cited

U.S. PATENT DOCUMENTS 6,334,708 B1 1/2002 Kosugi
7,433,503 B2 10/2008 Cherek
(Continued)

FOREIGN PATENT DOCUMENTS

DE 102012201798 A1 * 8/2013 ............. A61B 6/545
DE 102012201798 A1 8/2013
(Continued)

*Primary Examiner* — Mark R Gaworecki
(74) *Attorney, Agent, or Firm* — Larry Liberchuk

(57) ABSTRACT

The invention relates to a device (10) for imaging of an object (30), an X imaging system (1) for imaging of an object (30), a method for imaging of an object (30), a computer program element for controlling such device or system for performing such method and a computer readable medium having stored such computer program element. The device (10) comprises a provision unit (11) and a processing unit (12). The provision unit (11) is configured to provide position and orientation data of an object (30) to be imaged and to provide position and orientation data of an imaging unit (20) relative to a region of the object (30) and adjusted for a subsequent imaging of the region. The processing unit (12) is configured to combine the position and orientation data of the object (30) and the position and orientation data of the imaging unit (20) to determine the region to be subsequently imaged and to set at least one imaging parameter of the imaging unit (20) based on the determined region to be subsequently imaged.

12 Claims, 1 Drawing Sheet

(56) References Cited

U.S. PATENT DOCUMENTS

| | | |
|---|---|---|
| 7,627,084 B2 | 12/2009 | Jabri |
| 7,873,403 B2 | 1/2011 | Lachner |
| 8,223,915 B2 | 7/2012 | Borghese |
| 8,705,819 B2 | 4/2014 | Carlsen |
| 2002/0054662 A1 | 5/2002 | Verdonck |
| 2015/0104092 A1* | 4/2015 | Flohr .................. G06K 9/4604 382/131 |
| 2017/0340299 A1* | 11/2017 | Grass ...................... A61B 6/03 |

FOREIGN PATENT DOCUMENTS

| | | |
|---|---|---|
| WO | WO2012127117 A1 | 9/2012 |
| WO | WO2014033614 A1 | 3/2014 |

\* cited by examiner

DEVICE FOR IMAGING AN OBJECT

FIELD OF THE INVENTION

The invention relates to a device for imaging of an object, a system for imaging of an object, a method for imaging of an object, a computer program element for controlling such device or system for performing such method and a computer readable medium having stored such computer program element.

BACKGROUND OF THE INVENTION

In radiography, an anatomical region examined is known before the examination. Hence, it is possible to preselect an appropriate image processing in nearly all cases. Furthermore, in radiology there is usually a delay between examination and diagnosis, which gives a radiologist a possibility to change or adapt the image processing later on. On the contrary, in fluoroscopy, the anatomical region examined is often changing during the examination. This means that compared to radiology a more general image processing has to be applied to images of different anatomical regions. Such general image processing may be non-optimal for particular anatomical regions.

US 2010/183206 (A1) discloses an automatically adjusting acquisition protocol for dynamic medical imaging, such as dynamic CT, MRI or PET imaging. The protocols are adjusted based on anatomic and dynamic models which are individualized or fitted to each patient based on a scout scan. The adjustment can compensate for changes in the patient due to patient motion (e.g. breathing or heartbeat) or flow of contrast or tracing agent during the sequence. The dynamic model can be a motion model used to predict the motion of anatomic/physiologic features, typically organs, during scanning, or a haemodynamic model used to predict flow of the contrast agent allowing for precise timing of the scanning sequence.

DE 10 2012 201798A1 discloses a method for planning an X-ray imaging of an examination area of an object with low radiation exposure, comprising the following steps: S1) Receiving configuration parameters of the X-ray imaging device; S2) Determining the position of at least one part of the object; S3) Determining at least one irradiated region of the object that is imaged depending on the configuration parameters of the X-ray imaging device and the position of at least one part of the object. Furthermore, the invention describes a device for planning an X-ray imaging with low radiation exposure.

WO 2014/033614 A1 discloses an apparatus and method for automatically or semi-automatically controlling a collimator of an X-ray imager to collimate imager's X-ray beam and adjusting an alignment of the X-ray imager in respect of an object. The collimation and alignment operation is based on 3D image data of the object to be imaged. The 3D image data is acquired by a sensor. The sensor operates on non-ionizing radiation. The 3D image data describes a shape in 3D of the object and anatomic landmarks are derived therefrom to define a collimation window for a region of interest. Based on the collimation window the collimator's setting and imager alignment is adjusted accordingly.

The image processing may, however, still be improved.

SUMMARY OF THE INVENTION

Hence, there may be a need to provide a device for imaging of an object which allows an improved image processing.

The object of the present invention is solved by the subject-matters of the independent claims, wherein further embodiments are incorporated in the dependent claims. It should be noted that the aspects of the invention described in the following apply also to the imaging device, the imaging system, the imaging method, the computer program element, and the computer readable medium.

According to the present invention, a device for imaging of an object is presented. The imaging device comprises a provision unit and a processing unit. The provision unit is configured to provide position and orientation data of the object to be imaged. The provision unit is further configured to provide position and orientation data of an imaging unit adjusted for a subsequent imaging of a region of the object to be imaged. The processing unit is configured to combine the position and orientation data of the object and the position and orientation data of the imaging unit to determine the region to be subsequently imaged and to set at least one imaging parameter of the imaging unit based on the determined region to be subsequently imaged.

Herein position data as well as orientation data may be either two-dimensional ("2D") or three-dimensional ("3D"). For example, the position data may be provided in the form of coordinates along two or three mutually independent directions e.g. in 2D or 3D Cartesian space, respectively. Furthermore, the orientation data may for example be provided in the form of rotations along two or three mutually independent directions e.g. in 2D or 3D Cartesian space, respectively. In an example, the position data and orientation data employ a common (sub-)set of 2D or 3D directions. In another example, the position data and orientation data employ mutually different sets of 2D or 3D directions.

The processing unit is capable of determining i.e. predicting, based on a combination of the position data and orientation data of both the object and the imaging unit, the region to be subsequently imaged. While doing so, the processing unit does not need to rely on (yet may incorporate) information concerning the medical imaging protocol at hand. For example, the processing unit may be able to distinguish between a posterior-anterior ("PA") exposure and an anterior-posterior ("AP") exposure based on a combination of orientation data of the object with orientation data of the imaging unit. Furthermore, for example, the processing unit may be able to determine scan direction e.g. from head to toe or viceversa based on a combination of position data of the object and position data of the imaging unit. Furthermore, for example, the processing unit may be able to determine the region to be subsequently imaged based on the position data of the imaging unit and such scan direction.

A dynamic X-ray system, for example a fluoroscopy system, is configured for imaging a non-static region i.e. the region to be imaged is not constant over time. The device for imaging of an object according to the present invention particularly allows for successful clinical application in such dynamic X-ray system, either in diagnostic or interventional use. That is, the device according the present invention— owing to its capability to predict the region to be subsequently imaged and to set at least one imaging parameter based on such prediction—is advantageously capable of automatically selecting and setting, in dependence of the region to be subsequently imaged, an optimal i.e. most appropriate value for the at least one imaging parameter. Hence, the device for imaging of an object according to the present invention advantageously circumvents from selecting and/or setting a sub-optimal value for the at least one imaging parameter applicable to the entire object. Herein, imaging parameter includes the parameters concerning image processing as well as parameters concerning the imaging itself, e.g. parameters concerning irradiation such as generator voltage, tube pre-filtration and dose in case the imaging unit comprises an X-ray source.

In an example, the object to be imaged is a patient and the region to be subsequently imaged is an anatomical region.

In an example, the provision unit is configured to provide position and/or orientation data of the object and/or the imaging unit relative to the region of the object to be imaged. In another example, the provision unit is configured to provide absolute position and/or orientation data of the object and/or the imaging unit. Based on this information, the processing unit may be configured to calculate relative position and/or orientation data of the object and/or the imaging unit.

The imaging unit may be an X-ray system. In an example, the position and orientation data of the imaging unit comprise a position and an orientation of an X-ray tube, an X-ray detector and/or a collimator.

In an example, the provision unit is further configured to provide an anatomical model of the object, such anatomical model having one or more anatomical landmarks, and to provide the position and orientation data of the object by combining the anatomical model and the one or more anatomical landmarks. Preferably, at least three landmarks are used to estimate the position and orientation of an object in 3D space.

In an example, the anatomical model is preselected out of a group of anatomical models based on patient data and/or based on a previous image or a pre-scan of the object or the region to be subsequently imaged. Thereby the anatomical model for e.g. a child or an adult, or a slim, a normal or overweight patient can be preselected.

In an example, the anatomical model is adapted into an adapted anatomical model based on patient data and/or based on a previous image of the region to be subsequently imaged. Thereby, the anatomical model can be adapted to the patient at hand, for example a child or an adult, or a slim, a normal or an overweight patient.

In an example, the provision unit is further configured to detect the position of an anatomical landmark in patient data acquired by 2D and/or 3D optical, video, infrared and/or ultrasound means. Exemplarily, in case a position and orientation of the object to be imaged is stationary relative to the imaging unit and provided the orientation of an X-ray tube relative to an X-ray detector is known, a two-dimensional estimation of the anatomical landmark(s) may be sufficient. This estimation may be based on simple video images detecting an outline of the object to be imaged.

Exemplarily, the device for imaging of an object according to the invention may be part of a dynamic X-ray system i.e. fluoroscopy system in which imaging parameters are automatically selected based on the region to be imaged next. Herein, the region to be subsequently imaged is identified by combining the position and orientation data of the imaging unit with the position and orientation data of the object as derived from an anatomical model having anatomical landmarks, wherein the landmarks are calculated from a previous image or pre-scan e.g. using optical, infrared and/or ultrasound means.

In an example in which the device for imaging of an object is part of a dynamic X-ray system, the processing unit is configured for updating the anatomical model hence the anatomical landmarks based on a previous image as acquired by the dynamic X-ray system. That is, a dynamic X-ray system typically generates a range of images which allow for improving the precision and/or quality with which the position of the anatomical landmarks is determined by the processing unit.

According to the present invention, also a system for imaging of an object is presented. The imaging system comprises an imaging unit and the imaging device as described above. The imaging unit may comprise an X-ray source and an X-ray detector. Such X-ray source may comprise an X-ray tube driven by a high voltage generator. At least one imaging parameter of the imaging unit is set based on a region determined by the imaging device to be subsequently imaged.

According to the present invention, also a method for imaging of an object is presented. It comprises the following steps, not necessarily in this order:
 a) providing position and orientation data of an object to be imaged,
 b) providing position and orientation data of an imaging unit relative to a region of the object and adjusted for a subsequent imaging of the region,
 c) combining the position and orientation data of the object and the position and orientation data of the imaging unit to determine the region to be subsequently imaged, and
 d) setting at least one imaging parameter of the imaging unit based on the determined region to be subsequently imaged.

In an example, the method further comprises step e for imaging the determined region to be subsequently imaged.

In other words, the method for imaging of an object according to the invention may comprise the steps of:
 Acquisition of patient positioning information to estimate a position of anatomical landmarks.
 Matching an anatomical model to these landmarks to estimate the positions of anatomical regions.
 Using system information about a position and/or orientation of an X-ray tube, detector and/or collimation to determine a specific anatomical region irradiated during a next image acquisition.
 Selecting the most appropriate image processing for this anatomical region.
 Applying this image processing to the next image acquired.

According to the present invention, also a computer program element is presented, wherein the computer program element comprises program code means for causing the imaging system as defined in the independent claim to carry out the steps of the imaging method as defined in the independent claim when the computer program is run on a computer controlling the imaging system.

It shall be understood that the imaging device, the imaging system, the imaging method, the computer program element for controlling such device and the computer readable medium having stored such computer program element according to the independent claims have similar and/or identical preferred embodiments, in particular, as defined in the dependent claims. It shall be understood further that a preferred embodiment of the invention can also be any combination of the dependent claims with the respective independent claim.

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the accompanying drawings.

DETAILED DESCRIPTION OF EMBODIMENTS

Figure 1:
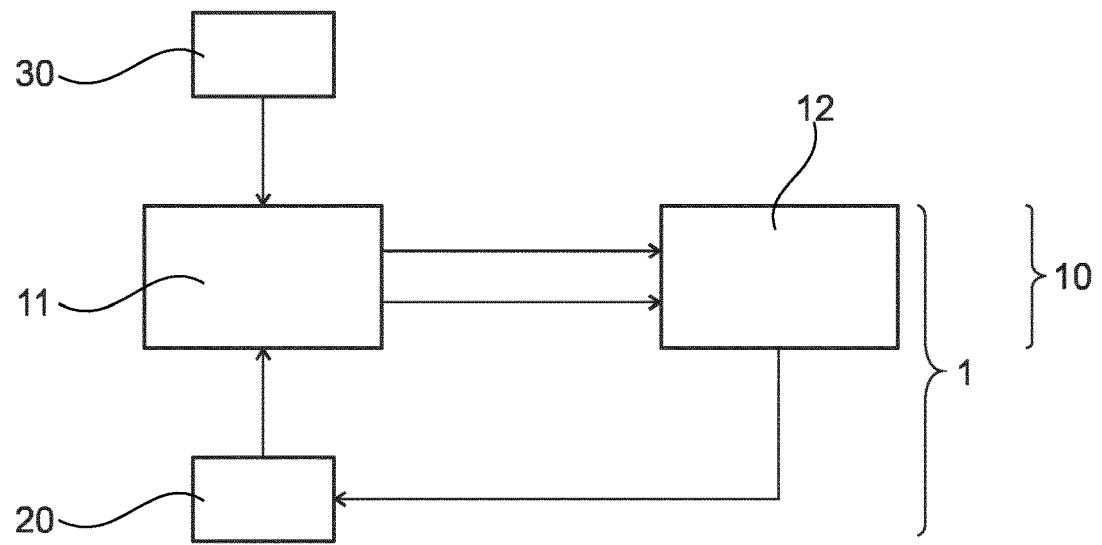
FIG. 1 shows a schematic drawing of an example of a system for imaging of an object according to the invention.

FIG. 1 shows schematically and exemplarily an embodiment of an imaging system 1 for an object 30 according to the invention. The object 30 to be imaged may be a patient and the region to be subsequently imaged may be an anatomical region. The imaging system 1 comprises an imaging unit 20 and an imaging device 10 for an object 30 to be imaged. The imaging unit 20 may comprise an X-ray tube. At least one imaging parameter of the imaging unit 20 is set based on a region determined by the imaging device 10 to be subsequently imaged. The imaging device 10 comprises a provision unit 11 and a processing unit 12.

The provision unit 11 provides position and orientation data of an object 30 to be imaged and position and orientation data of an imaging unit 20 relative to a region of the object 30. The imaging unit 20 is adjusted for a subsequent imaging of the region.

The position and orientation data of the object 30 may comprise positions of anatomical landmarks of the object 30 and the provision unit 11 may be configured to provide an anatomical model and to combine the anatomical model and the positions of the object's anatomical landmarks to provide the position and orientation data of the object 30. The provision unit may further detect the position of an anatomical landmark in patient data acquired by 2D and/or 3D optical, video, infrared and/or ultrasound means.

The position and orientation data of the imaging unit 20 may comprise a position and an orientation of an X-ray tube, an X-ray detector and a collimator. The processing unit 12 combines the position and orientation data of the object 30 and the position and orientation data of the imaging unit 20 to determine the region to be subsequently imaged and to set at least one imaging parameter of the imaging unit 20 based on the determined region to be subsequently imaged.

Thereby, the imaging device 10 according to the invention automatically sets the most appropriate imaging parameter(s) and thereby the most appropriate image processing for the next and thereby for all subsequent anatomical regions being imaged.

The imaging device 10 according to the invention may not only be used to adapt the image processing but also to improve the irradiation by the imaging unit 20. The imaging unit 20 may comprise an X-ray tube and the processing unit 12 may set an irradiation parameter of the imaging unit 20 based on the determined region to be subsequently imaged. Thereby, X-ray beam quality (e.g. generator kV, tube pre-filtration) and dose (generator mAs) settings may be set based on information about the anatomy irradiated during the next image acquisition.

Figure 2:
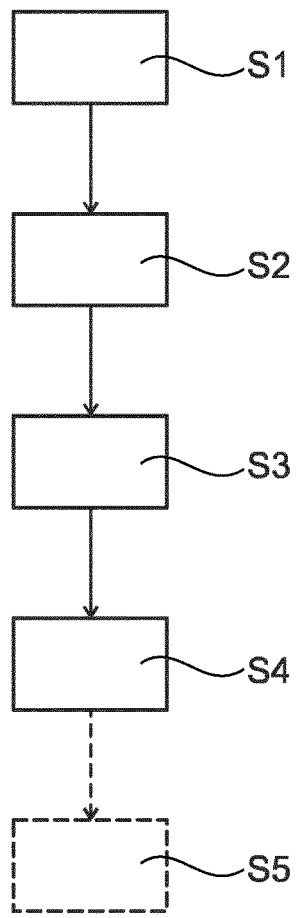
FIG. 2 shows basic steps of an example of a method for imaging of an object.

FIG. 2 shows a schematic overview of steps of a method for imaging of an object 30. The method comprises the following steps, not necessarily in this order:

In a first step S1, providing position and orientation data of an object 30 to be imaged.

In a second step S2, providing position and orientation data of an imaging unit 20 relative to a region of the object 30 and adjusted for a subsequent imaging of the region.

In a third step S3, combining the position and orientation data of the object 30 and the position and orientation data of the imaging unit 20 to determine the region to be subsequently imaged.

In a fourth step S4, setting set at least one imaging parameter of the imaging unit 20 based on the determined region to be subsequently imaged.

In an optional fifth step S5, imaging the determined region to be subsequently imaged.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfil the procedure of an exemplary embodiment of the method as described above.

According to a further exemplary embodiment of the present invention, a computer readable medium, such as a CD-ROM, is presented wherein the computer readable medium has a computer program element stored on it, which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A device for imaging an object, comprising:
a provision unit configured to provide position and orientation data of the object to be imaged, the provision unit being configured to provide an anatomical model of the object, the anatomical model having one or more anatomical landmarks, and to provide the position and orientation data of the object by combining the anatomical model and the one or more anatomical landmarks, wherein the provision unit is further configured to provide position and orientation data of an imaging unit adjusted for a subsequent imaging of a region of the object to be imaged; and
a processing unit configured to combine the position and orientation data of the object and the position and orientation data of the imaging unit to determine the region to be subsequently imaged, wherein the processing unit is further configured to set at least one imaging parameter of the imaging unit based on the determined region to be subsequently imaged, wherein the anatomical model is preselected out of a group of anatomical models based on a previous image of the region to be subsequently imaged.

2. The device according to claim 1, wherein the object to be imaged is a patient and the region to be subsequently imaged is an anatomical region.

3. The device according to claim 1, wherein the provision unit is further configured to provide position and/or orientation data of the imaging unit relative to the region of the object to be imaged.

4. The device according to claim 1, wherein the provision unit is further configured to detect positions and/or orientations of the anatomical landmarks in patient data acquired by one of: 2D and/or 3D optical, video, infrared and/or ultrasound.

5. The device according to claim 1, wherein the anatomical model is preselected out of a group of anatomical models based on patient data.

6. The device according to claim 1, wherein the anatomical model is adapted into an adapted anatomical model based on patient data and/or based on a previous image of the region to be subsequently imaged.

7. The device according to claim 1, wherein the position and orientation data of the imaging unit comprise a position and an orientation of one of: an X-ray tube, an X-ray detector and/or a collimator.

8. The device according to claim 1, wherein the processing unit is further configured to set an irradiation parameter of the imaging unit based on the determined region to be subsequently imaged.

9. A system for imaging an object, comprising:
an imaging unit; and
a device for imaging the object, comprising:
a provision unit configured to provide position and orientation data of the object to be imaged, the provision unit being configured to provide an anatomical model of the object, the anatomical model having one or more anatomical landmarks, and to provide the position and orientation data of the object by combining the anatomical model and the one or more anatomical landmarks, wherein the provision unit is further configured to provide position and orientation data of an imaging unit adjusted for a subsequent imaging of a region of the object to be imaged; and
a processing unit configured to combine the position and orientation data of the object and the position and orientation data of the imaging unit to determine the region to be subsequently imaged, the processing unit being configured to set at least one imaging parameter of the imaging unit based on the determined region to be subsequently imaged, wherein the anatomical model is preselected out of a group of anatomical models based on a previous image of the region to be subsequently imaged,
wherein at least one imaging parameter of the imaging unit is set based on a region to be subsequently imaged.

10. A method for imaging an object, comprising:
providing position and orientation data of the object to be imaged;
preselecting an anatomical model out of a group of anatomical models based on a previous image of the region to be subsequently imaged, the anatomical model having one or more anatomical landmarks;
providing the position and orientation data of the object by combining the anatomical model and the one or more anatomical landmarks;
providing position and orientation data of an imaging unit adjusted for a subsequent imaging of the region;
combining the position and orientation data of the object and the position and orientation data of the imaging unit to determine the region to be subsequently imaged; and
setting at least one imaging parameter of the imaging unit based on the determined region to be subsequently imaged.

11. The method according to claim 10, further comprising imaging the determined region to be subsequently imaged.

12. A non-transitory computer readable medium having one or more executable instructions stored thereon, which when executed by a processor, cause the processor to perform a method for imaging an object, the method comprising:
providing position and orientation data of the object to be imaged;
preselecting an anatomical model out of a group of anatomical models based on a previous image of the region to be subsequently imaged, the anatomical model having one or more anatomical landmarks;
providing the position and orientation data of the object by combining the anatomical model and the one or more anatomical landmarks;

providing position and orientation data of an imaging unit adjusted for a subsequent imaging of the region;

combining the position and orientation data of the object and the position and orientation data of the imaging unit to determine the region to be subsequently imaged; and setting at least one imaging parameter of the imaging unit based on the determined region to be subsequently imaged.

* * * * *